United States Patent [19]

Machida et al.

[11] Patent Number: 6,013,831

[45] Date of Patent: *Jan. 11, 2000

[54] PROCESSES FOR THE PRODUCTION OF HIGH-PURITY DIMETHYL 2, 6-NAPHTHALENEDICARBOXYLATE AND NAPHTHALENEDICARBOXYLIC ACID

[75] Inventors: Hiroshi Machida; Fumiya Zaima; Kengi Nakaya; Kazuo Tanaka, all of Kurashiki, Japan

[73] Assignee: Mitsubishi Gas Chemical Company, Inc., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/069,815

[22] Filed: Apr. 30, 1998

[30] Foreign Application Priority Data

May 8, 1997 [JP] Japan ..................................... 9-118163
Jul. 11, 1997 [JP] Japan ..................................... 9-186882

[51] Int. Cl.[7] ..................................................... C07C 67/48
[52] U.S. Cl. ................................................. 560/78
[58] Field of Search ................................................. 560/78

[56] References Cited

U.S. PATENT DOCUMENTS 4,886,901  12/1989  Holzhauer et al. .
5,183,933   2/1993  Harper et al. .
5,262,560  11/1993  Holzhauer et al. ..................... 560/78

FOREIGN PATENT DOCUMENTS 0 450 621  10/1991  European Pat. Off. .
0 721 931   7/1996  European Pat. Off. .

OTHER PUBLICATIONS

*Patent Abstracts of Japan*, 17(232) (C–1056), abstract of JP 4–364152 (May 1993).

*Primary Examiner*—Samuel Barts
*Attorney, Agent, or Firm*—Wenderoth, Lind & Ponack, L.L.P.

[57] ABSTRACT

A process for the production of high-purity dimethyl 2,6-naphthalenedicarboxylate, which comprises esterifying 2,6-naphthalenedicarboxylic acid obtained by liquid phase oxidation of 2,6-dialkylnaphthalene with molecular oxygen in the presence of an oxidation catalyst, with methanol and then purifying a crude ester formed by the esterification, the crude ester being purified in the presence of an aromatic hydrocarbon as a solvent, in which impurities contained in a reaction product obtained by the esterification of 2,6-naphthalenedicarboxylic acid prepared by the liquid phase oxidation of 2,6-dialkylnaphthalene are effectively removed with simple procedures, oxidation catalyst metals are recovered, a crystal of naphthalenedicarboxylic acid formed by the oxidation of dialkylnaphthalene and/or its oxide derivative can be easily separated, and the oxidation catalyst to be brought into the step of producing dimethyl naphthalenedicarboxylate is recovered in the process of the production of naphthalenedicarboxylic acid and effectively used in the process of the production of naphthalenedicarboxylic acid.

18 Claims, 1 Drawing Sheet

PROCESSES FOR THE PRODUCTION OF HIGH-PURITY DIMETHYL 2, 6-NAPHTHALENEDICARBOXYLATE AND NAPHTHALENEDICARBOXYLIC ACID

BACKGROUND OF THE INVENTION

1. Field of the Invention

The present invention relates to a process for the production of dimethyl 2,6-naphthalenedicarboxylate and a process for the production of naphthalenedicarboxylic acid. More specifically, it relates to a process for the production of a process for the production of high-purity dimethyl 2,6-naphthalenedicarboxylate (to be sometimes referred to as "2,6-NDCM" hereinafter), in which 2,6-naphthalenedicarboxylic acid (to be sometimes referred to as "2,6-NDCA" hereinafter) obtained by liquid phase oxidation is esterified with methanol and then resultant ester is purified (to be referred to as "present specification 1" hereinafter), and a process for the production of naphthalenedicarboxylic acid (to be sometimes referred to as "NDCA" hereinafter) by oxidizing dialkylnaphthalene and/or its oxide derivative, in which process naphthalenedicarboxylic acid having an improved crystal grain size is produced (to be referred to as "present invention 2").

2. Prior Art of the Invention

NDCA and NDCM, 2,6-NDCA and 2,6-NDCM in particular, are useful materials as materials for a high-function polyester.

Related art to the present invention 1 will be explained below.

2,6-NDCA is obtained by a method in which 2,6-dialkylnaphthalene is oxidized in a solvent containing a lower aliphatic carboxylic acid in the presence of an oxidation catalyst containing cobalt, manganese and bromine (JP-B-34-2666 and JP-B-56-3337).

2,6-NDCA obtained by the above method contains organic impurities such as trimellitic acid, 6-formyl-2-naphthoic acid, etc., and heavy metals such as cobalt, manganese, etc., from the catalyst. 2,6-NDCA can be suitably used as a material for a high-function polymer only after the above impurities, etc., are removed. Since, however, 2,6-NDCA has a low solubility in a solvent and is decomposed at its melting point, it is difficult to purify 2,6-NDCA while it remains intact.

There have been therefore proposed many methods in which 2,6-NDCA is esterified with methanol to form 2,6-NDCM and then 2,6-NDCM is distilled and/or recrystallized. For obtaining particularly high-quality 2,6-NDCM, it is effective to employ a method in which the purification is carried out by a combination of distillation and recrystallization (JP-A-50-116461, U.S. Pat. No. 5,262,560, JP-B-57-35697 and JP-B-46-9697).

Further, the above heavy metals such as cobalt, manganese, etc., contained in 2,6-NDCA are expensive, and it is industrially preferred to recover and recycle them.

The method of recovering oxidation catalyst metals contained in 2,6-NDCA is largely classified to a method in which 2,6-NDCA crystals are washed with a solvent such as a mineral acid aqueous solution or an alcohol containing an acid component to elute a metal content and the metal content is recovered (JP-A-62-212345 and JP-A-5-253496) and a method in which 2,6-NDCA is esterified and the heavy metals are recovered from the reaction mixture (JP-A-3-223233 and JP-A-4-364152).

When the former method in which 2,6-NDCA crystals are washed with a solvent to elute catalyst metals is used as a method for recovering the oxidation catalyst contained in 2,6-NDCA, there is required an apparatus for separating a wash liquid and the 2,6-NDCA crystals. There is another method for recovering a metal content from a wash liquid, in which a carbonic acid compound is added to form an insoluble carbonate. However, there is required a solid-liquid separation apparatus for separating a precipitate of the above insoluble carbonate, and the apparatus is complicated. Further, the ratio of removal of the metal content by the washing is not so high, so that the washed 2,6-NDCA still contains a large amount of metals, and it is further required to remove the metal content by some other purification method.

On the other hand, in the method of JP-A-3-223233 which uses means of recovering the catalyst metals from a crude ester obtained by esterification of 2,6-NDCA, the oxidation catalyst metals are dissolved in a solvent by using, as a catalyst, a mineral acid such as sulfuric acid for the esterification. Then, a compound which generates carbonate ion is added to mother liquor from which the esterification product is separated, and the catalyst metals are recovered in the form of an insoluble carbonate. The above method has problems that reactor materials are limited due to the corrosiveness of the mineral acid such as sulfuric acid and that it is required to treat waste acid by neutralization. The above method is therefore not suitable for use in a large-scale industrial plant.

In the method disclosed in JP-A-4-364152, insoluble oxidation catalyst metals are separated from the esterification product in a molten state or a solution thereof in methanol by filtration or centrifugalization.

For maintaining the esterification product in a molten state, however, it is required to heat the esterification product to a temperature equivalent to, or higher than, the melting point (about 190° C.) of 2,6-NDCA, and it is technically very difficult to separate and recover the insoluble catalyst metals from the molten liquid by filtration and centrifugalization on an industrial scale.

In the method of separating the insoluble oxidation catalyst metals from the methanol solution, the solubility of 2,6-NDCM is very low at the boiling point of methanol as shown in Examples to be described later, and it is therefore required to heat the methanol solution to a temperature higher than the boiling point of methanol under elevated pressure in order to dissolve the esterification product containing 2,6-NDCM as a main component in an industrially practical amount of a solvent. Further, it is also required to separate the catalyst metals under the above elevated pressure, and the cost for facilities required therefor increases.

Further, the present inventor's studies have revealed the following. A crystal of 2,6-NDCM obtained by recrystallization from the methanol solution has the form of scales and has a small bulk density, and it brings a large amount of mother liquor into a cake when the solid-liquid separation is carried out by a method of filtration or centrifugalization, so that no sufficient effect of removing impurities can be obtained.

Related art of the present invention 2 will be explained below.

There have been proposed various methods for producing NDCA by oxidizing dialkylnaphthalene and/or its oxide derivative with molecular oxygen. However, the crystal of crude NDCA obtained in any one of these methods has a small diameter. Further, since NDCA has a low solubility in a reaction solvent, it is difficult to increase the particle size of NDCA much even if multi-staged crystallization is carried out in the same manner as in the process for the production of terephthalic acid. There is therefore a problem that solid-liquid separation, particularly, solid-liquid separation with an industrially advantageous centrifugal separator, is very difficult in the step of separating reaction mother liquor or the step of washing subsequent thereto.

For increasing the size of the above NDCA and improving its separability, JP-A-50-121225 discloses a method in which a slurry obtained after the reaction is maintained at a temperature between 20° C. and 100° C. for at least 4 hours for crystal aggregation.

Further, JP-A-6-65143 discloses that the particle diameter of NDCA is increased by carrying out the oxidation in a specific temperature range (180 to 220° C.).

JP-A-6-293697 discloses that fine crystals of NDCA contained reaction mother liquor and a filtrate from the washing is again fed to an oxidation reactor so that the fine crystals are grown so as to have a particle size suitable for solid-liquid separation.

Generally, since NDCA formed by the oxidation has a very small particle size, it is difficult to separate a crystal of NDCA and a solvent. Further, cobalt and manganese used as a reaction catalyst are inevitably brought into the step of producing NDCM, and their recovery is required.

According to the studies the present inventors have made, in the methods of increasing the particle size of NDCA crystals, described in JP-A-50-121255 and JP-A-6-65143, the obtained NDCA crystal are crystals having the form of a plate, a strap or an aggregate of plates or straps, and the crystals are easily crushable and are easily crushed into fine pieces when the slurry is transported with a pump, etc., so that it is difficult to fully separate the crystals.

Further, it has been found that when reaction mother liquor containing fine particles is repeatedly continuously recycled to an oxidation reactor according to the method described in JP-A-6-293697, the amount ratio of fine crystals in a slurry fed to the solid-liquid separation step gradually increases, which results in no performance of solid-liquid separation.

SUMMARY OF THE INVENTION

It is an object of the present invention 1 to provide a process for the production of high-purity 2,6-NDCM, in which impurities contained in a reaction product obtained by the esterification of 2,6-NDCA prepared by the liquid phase oxidation of 2,6-dialkylnaphthalene are effectively removed with simple procedures.

It is further another object of the present invention 1 to provide a process for industrially advantageously producing 2,6-NDCM by recovering oxidation catalyst metals in the above process.

Further, it is an object of the present invention 2 to provide a process for the production of NDCA, in which a crystal of NDCA formed by the oxidation of dialkylnaphthalene and/or its oxide derivative can be easily separated.

Further, it is another object of the present invention 2 to provide a process for the production of NDCA, in which an oxidation catalyst to be brought into the step of producing NDCM is recovered in the above process of the production of NDCA and effectively used in the process of the production of NDCA.

According to the present invention 1, there is provided a process for the production of high-purity 2,6-NDCM, which comprises esterifying 2,6-naphthalenedicarboxylic acid obtained by liquid phase oxidation of 2,6-dialkylnaphthalene with molecular oxygen in the presence of an oxidation catalyst, with methanol and then purifying a crude ester obtained by the esterification, the crude ester being purified in the presence of an aromatic hydrocarbon as a solvent.

According to the present invention 1, there is provided a process for the production of high-purity dimethyl 2,6-naphthalenedicarboxylate, which comprises mixing the crude ester formed by the esterification in the above process with an aromatic hydrocarbon solvent, heating the mixture to dissolve the crude ester in the aromatic hydrocarbon solvent, removing an insoluble contained in the solution of the crude ester by filtering or centrifugalizing, cooling a solution of the crude ester after the removal of the insoluble, to recrystallize and separate dimethyl 2,6-naphthalenedicarboxylate, and distilling the separated crystal of dimethyl 2,6-naphthalenedicarboxylate under reduced pressure to remove contents having high-boiling points. In the above process for the production of high-purity dimethyl 2,6-naphthalenedicarboxylate, further, the contents having high boiling points may be recycled to the esterification step.

According to the present invention 1, there is also provided a process for the production of high-purity 2,6-NDCM, which comprises distilling the crude ester crystal formed by the esterification in the above process, under reduced pressure to remove contents having high boiling points and recrystallizing distillate 2,6-NDCM in an aromatic hydrocarbon solvent to purify the 2,6-NDCM.

According to the present invention 1, there is also provided a process for the production of high-purity dimethyl 2,6-naphthalenedicarboxylate, which comprises mixing the contents having high boiling points separated in the above process with an aromatic hydrocarbon solvent, heating the mixture to dissolve the contents in the aromatic hydrocarbon solvent, removing an insoluble in the solution by filtering or centrifugalizing, cooling the resultant solution free of the insoluble to precipitate a crystal of dimethyl 2,6-naphthalenedicarboxylate and recovering the dimethyl 2,6-naphthalenedicarboxylate.

According to the present invention 1, further, there is provided a process for the production of high-purity dimethyl 2,6-naphthalenedicarboxylate, which comprises separating and recovering the oxidation catalyst contained in the crude ester in the above process, as a substance insoluble in an aromatic hydrocarbon solvent, and recycling the recovered insoluble substance as a catalyst source for the oxidation.

According to the present invention 2, there is provided a process for the production of naphthalenedicarboxylic acid, which comprises oxidizing dialkylnaphthalene and/or its oxide derivative with an oxygen-containing gas in a solvent containing a lower aliphatic carboxylic acid in the presence of an oxidation catalyst composed of heavy metals containing at least cobalt and manganese and bromine, the oxidation being carried out using, as a catalyst component, a naphthalenedicarboxylic acid metal salt in the form of a solid.

In the above process for the production of naphthalenedicarboxylic acid according to the present invention 2, further, the naphthalenedicarboxylic acid containing the oxidation catalyst may be esterified, and the naphthalenedicarboxylic acid metal salt is recovered from an obtained ester and recycled to the oxidation.

In the above process for the production of naphthalenedicarboxylic acid according to the present invention 2, the naphthalenedicarboxylic acid metal salt may be added in an amount of 0.5 to 20% by weight based on the total amount of the dialkylnaphthalene and/or its oxide derivative.

DETAILED DESCRIPTION OF THE INVENTION

Figure 1:
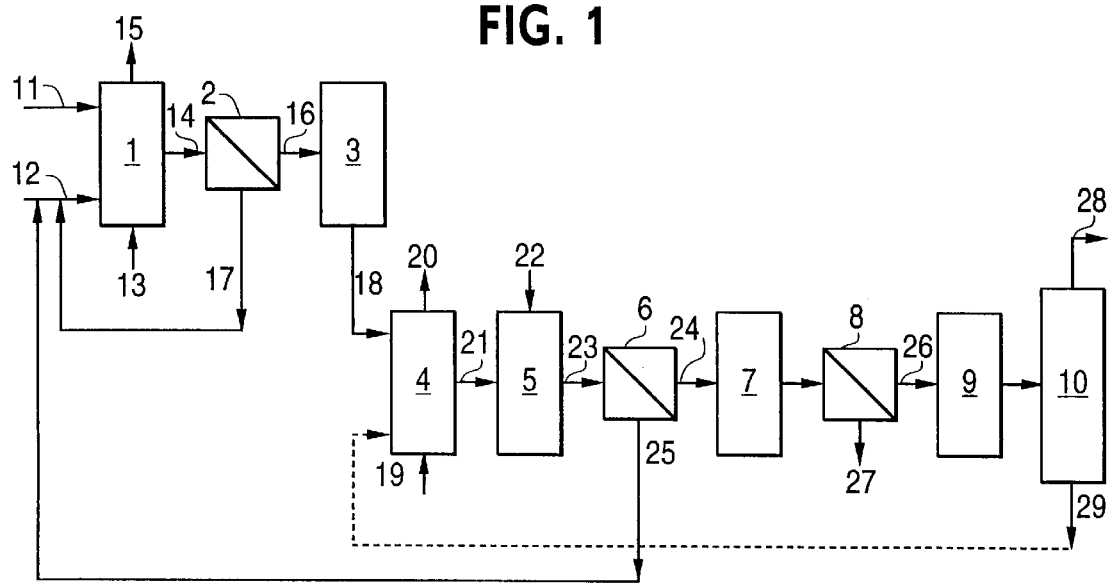
FIG. 1 shows a flow chart of a case where a crude ester from which insoluble catalyst metals are removed is purified and then purified by distillation according to a method (A) in the present invention 1.

The present inventors have made diligent studies of methods of purifying 2,6-NDCA by the esterification of the 2,6-NDCA with methanol and, as a result, have found the following. When 2,6-NDCA is purified by recrystallization in the presence of an aromatic hydrocarbon as a solvent, 2,6-NDCA having excellent qualities can be obtained. When an insoluble oxidation catalyst content contained in an esterification product from 2,6-NDCA is recovered, an oxidation catalyst metal salt can be easily recovered at a high yield by dissolving the esterification product or contents having high boiling points obtained by distilling the esterification product in an aromatic hydrocarbon as a solvent and treating the resultant solution by filtering or centrifugal precipitation. The present invention 1 has been thus arrived at.

That is, the present invention is directed to a process for the production of high-purity dimethyl 2,6-naphthalenedicarboxylate by oxidizing 2,6-dialkylnaphthalene with molecular oxygen in a liquid phase oxidation, to obtain 2,6-naphthalenedicarboxylic acid, esterifying the 2,6-naphthalenedicarboxylic acid with methanol to obtain a crude ester and purifying the crude ester, wherein the crude ester is purified in the presence of an aromatic hydrocarbon as a solvent.

The present inventors have made diligent studies for obtaining NDCA having a large particle diameter and as a result, have found the following. When dialkylnaphthalene and/or its oxide derivative are/is oxidized, NDCA crystals are grown to have a spherical form a large size and is grown to have a large bulk density by supplying a naphthalenedicarboxylic acid metal salt in the form of a slurry to an oxidation step, so that there can be obtained a crystal which easily permits solid-liquid separation and is easily transported. Further, in the step of esterification of NDCA, a trimellitic acid metal salt which is brought together with NDCA is converted to a naphthalenedicarboxylic metal salt, so that the metal salt can be effectively recovered or recycled as a catalyst component by separating the naphthalenedicarboxylic metal salt and supplying it in the form of a slurry to the oxidation step. The present invention 2 has been thus arrived at.

Specifically, in the present invention 1, the process for the production of high-purity 2,6-NDCM comprises oxidizing 2,6-dialkylnaphthalene with a gas containing molecular oxygen in a solvent containing a low aliphatic carboxylic acid in the presence of a catalyst composed of a heavy metal compound and a bromine compound, to prepare 2,6-NDCA, esterifying the 2,6-NDCA with methanol to obtain a crude ester, and purifying the crude ester by recrystallization and distillation, and the present invention 1 has a characteristic feature in that an aromatic hydrocarbon is used as a solvent for the separation of an insoluble contained in the crude ester and the recrystallization of the crude ester.

The process for the production of high-purity 2,6-NDCM according to the present invention 1 comprises ① the step of oxidizing 2,6-dialkylnaphthalene to obtain 2,6-NDCA, ② the step of esterifying the 2,6-NDCA to obtain a crude ester, ③ the step of dissolving the crude ester, ④ the steps of separating insolubles, ⑤ the step of recrystallization and ⑥ the step of distillation.

In the present invention 2 for the production of naphthalenedicarboxylic acid having an improved crystal particle size, the process for the production of naphthalenedicarboxylic acid comprises oxidizing dialkylnaphthalene and/or its oxide derivative with an oxygen-containing gas in a solvent containing a lower aliphatic carboxylic acid in the presence of a catalyst composed of a heavy metal oxidation catalyst and bromine, wherein a naphthalenedicarboxylic acid metal salt in the form of a solid is introduced as a catalyst component into the step of the oxidation. The process of the present invention 2 further comprises esterifying the naphthalenedicarboxylic containing the oxidation catalyst to obtain an ester, recovering a naphthalenedicarboxylic acid metal salt from the ester and recycling the naphthalenedicarboxylic acid metal salt to the oxidation.

Each step will be explained in detail hereinafter.

(Oxidation step)

The dialkylnaphthalene used as a raw material for the oxidation in the present invention includes dimethylnaphthalene, diethylnaphthalene and diisopropylnaphthalene. The oxide derivative thereof includes oxidation intermediates of the above dialkylnapthalenes such as formylnaphthoic acid and acetylnaphthoic acid, alkylacylnaphthalenes such as methyl acetylnaphthalene and methylbutylylnaphthalene, and diacylnaphthalene. Of the above dialkylnaphthalenes and oxide derivatives thereof, 2,6-substituted compounds are industrially useful. The 2,6-dialkylnaphthalene includes 2,6-dimethylnaphthalene, 2,6-dietnylnaphthalene and 2,6-diisopropylnaphthalene.

The solvent for the oxidation is preferably selected from lower aliphatic carboxylic acids such as formic acid, acetic acid, propionic acid and butyric acid, and acetic acid is the most preferred. While the solvent may contain water, the content thereof is 30% by weight or less. The amount of the solvent based on the weight of the dialkylnaphthalene as a raw material for the oxidation, such as 2,6-dialkylnaphthalene, is 1 to 20 times, preferably 3 to 10 times.

As a heavy metal oxidation catalyst used for the oxidation, a cobalt compound, a manganese compound and a bromine compound are used. Compounds of heavy metals such as iron, cerium and nickel may be added as required.

The above compounds of cobalt, manganese, iron, cerium and nickel include organic acid salts, hydroxides, halides and carbonates. An acetic acid salt and a bromide are particularly preferred. The bromine compound may be any compound so long as it is dissolved in a reaction system to generate bromide ion. The bromine compound includes inorganic bromides such as hydrogen bromide, sodium bromide, cobalt bromide and manganese bromide and organic bromides such as tetrabromoethane. Hydorgen bromide, cobalt bromide and manganese bromide are particularly preferred.

The metal catalyst is used in such an amount that the molar ratio of the total amount of heavy metal components including cobalt and manganese to the amount of the dialkylnaphthalene as an oxidation material, such as 2,6-dialkylnaphthalene and its oxide derivative, is 0.02 to 0.5, preferably 0.03 to 0.3, more preferably 0.04 to 0.2. Further, the bromine is used in such an amount that the molar ratio of bromine to the oxidation material is 0.01 to 0.3, preferably 0.015 to 0.15, more preferably 0.02 to 0.1.

The molecular-oxygen-containing gas used for the oxidation includes oxygen gas and a mixture prepared by mixing oxygen gas with an inert gas such as nitrogen or argon. Air is the most generally used.

The temperature for the oxidation is 170 to 250° C., preferably 180 to 240° C., more preferably 190 to 230° C. When the oxidation temperature is low, the amount of an intermediate increases, and the purity of NDCA decreases. When the temperature is too high, the combustion loss of the lower aliphatic carboxylic acid as a solvent increases, and the yield of NDCA decreases.

The pressure for the oxidation is 5 to 40 kg/cm$^2$G, preferably 10 to 30 kg/cm$^2$G.

The oxidation can be carried out by any one of a batch method, a semi-batch method and a continuous method.

A reactor for the oxidation is provided with a reflux condenser for condensing a large amount of the solvent which is brought together with a discharged gas and water formed by the oxidation. While the condensed solvent and the water are generally recycled to the reactor, part of them is withdrawn from the reaction system for adjusting the water concentration in the reactor. The oxygen concentration of the discharged gas from the reactor is 0.1 to 8% by volume, preferably 1 to 5% by volume.

2,6-NDCA crystals formed by the oxidation are separated from the solvent with a solid-liquid separator. The separator includes a centrifugal precipitator, a centrifugal filter and a vacuum filter.

The minimum size of crystals that can be separated with the above separator is generally 5 μm or larger when a decanter-type centrifugal precipitator is used, and it is 10 μm to 20 μm or more when a centrifugal filter or a vacuum filter is used. In the present invention 2, the obtained NDCA crystals have a size of at least 15 μm by introducing a naphthalenedicarboxylic acid metal salt in the form of a solid. That is, NDCA crystals obtained according to the present invention 2 are suitable for its separation with any one of the above separators.

The present invention 2 has a characteristic feature in that a naphthalenedicarboxylic acid metal salt is used as a catalyst for the oxidation of dialkylnaphthalene, etc.

The naphthalenedicarboxylic acid metal salt includes cobalt naphthalenedicarboxylate, manganese naphthalenedicarboxylate, cerium naphthalenedicarboxylate and nickel naphthalenedicarboxylate.

The above naphthalenedicarboxylic acid metal salt is supplied in the form of a solid and in the form of a slurry in a solvent such as acetic acid.

As a naphthalenedicarboxylic acid metal salt for use in the present invention 2, preferred is a salt which is recovered in the esterification of NDCA.

That is, when dialkylnaphthalene and/or its oxide derivative are/is oxidized to obtain NDCA, trimellitic acid is formed as a byproduct, and it forms a complex with a heavy metal in the solvent. The thus-formed trimellitic acid metal salt is difficult to separate from NDCA, and it is brought into the esterification step. When the NDCA is esterified with methanol, the trimellitic acid metal salt is converted to a naphthalenedicarboxylic acid metal salt, and the naphthalenedicarboxylic acid metal salt is separated by filtration or centrifugalization as an insoluble in a solvent such as an aromatic hydrocarbon used in the step of purification of the crude ester.

The particle diameter of the thus-obtained naphthalenedicarboxylic acid metal salt is as small as 2 to 5 μm. However, when the above naphthalenedicarboxylic acid metal salt is used for the oxidation, NDCA comes to have a uniform crystal particle size distribution, and further, the naphthalenedicarboxylic acid metal salt also effectively works as a catalyst for the oxidation.

The naphthalenedicarboxylic acid metal salt may be used alone or it may be used in combination with other organic acid salt, halide or carbonate.

The amount of the naphthalenedicarboxylic acid metal salt based on the dialkylnaphthalene and/or its oxide derivative is 0.2 to 30% by weight, preferably 0.5 to 20% by weight. When the above amount is too small, there is not much effect on the improvement of particle diameters. When it is too large, the result is rather worse.

(Esterification step)

In the present invention, the esterification of NDCA such as 2,6-NDCA with methanol can be carried out by any known method. For example, preferred is a method in which 2,6-NDCM in a molten state is used as a solvent and vaporized methanol is supplied to a slurry prepared by dispersing a crystal of 2,6-NDCA in the 2,6-NDCM.

The esterification is preferably carried out by a semi-continuous method or a continuous method.

In the semi-continuous method, NDCA and NDCM such as 2,6-NDCA and 2,6-NDCM are charged into a reactor and heated to a predetermined temperature to form a liquid phase, vaporized methanol is continuously supplied to the liquid phase and excessive vaporized methanol is continuously withdrawn from a gaseous phase portion of the reactor together with water formed by the reaction so as to maintain a constant pressure.

In the continuous method, NDCA such as 2,6-NDCA is dispersed in NDCM such as 2,6-NDCM in a molten state to form a slurry, the slurry is continuously supplied, and a reaction product is continuously withdrawn. Methanol is supplied to a liquid phase similarly to the semi-continuous method, and excessive methanol is withdrawn from a gaseous phase together with water formed by the reaction. For obtaining 2,6-NDCM at high reaction yields, preferably, at least two vessel-shaped reactors are used and 2,6-NDCA and methanol are brought into contact countercurrently, or a plate column or a bubble cup column of which the inside is divided in multi-stages is used and a liquid and a gas is brought into contact countercurrently.

The temperature for the esterification is 190 to 320° C., preferably 230 to 300° C., and the pressure for the esterification is 2 to 40 kg/cm$^2$G, preferably 10 to 30 kg/cm$^2$G.

As a catalyst for the esterification, it is preferred to use a molybdenum compound such as molybdenum trioxide. However, when the reaction is carried out at a high temperature of 240° C. or higher, the esterification can be carried out in the absence of a catalyst. The use of a mineral acid such as sulfuric acid is not preferred, since it makes the oxidation metal catalyst soluble.

As a solvent for the esterification, NDCM such as 2,6-NDCM is used, and part of the crude ester obtained by the esterification is recycled. The amount of the crude ester to be recycled is properly 2 to 6 times the weight of 2,6-NDCA.

For improving the yield of NDCM such as 2,6-NDCM, it is preferred to use methanol in an amount greater than its stoichiometric amount, and the molar ratio of methanol to supplied 2,6-NDCM is 5 to 40, preferably 10 to 25.

In the semi-continuous method, excessive methanol contained in a reaction product is removed by evaporation by reducing the pressure of the reactor to atmospheric pressure, and in the continuous method, excessive methanol contained in a reaction product is removed by evaporation by withdrawing the reaction product into a vessel held under atmospheric pressure conditions, whereby a crude ester in a molten state can be obtained.

According to the above reaction methods, 2,6-NDCM can be obtained at high yields under relatively low reaction pressure by the use of a small amount of methanol. Further, since methanol contained in the reaction product can be easily removed, a crude ester suitable for use in the subsequent purification step can be obtained.

The present invention 2 is a process for the production of NDCA, in which a naphthalenedicarboxylic acid metal salt is used as a catalyst component for the oxidation of dialkylnaphthalene and/or its oxide derivative. A trimellitic acid metal salt formed in the above oxidation is converted to trimethyl trimellitate and a naphthalenedicarboxylic acid metal salt in the process of esterification of NDCA. NDCM is separated and purified by recrystallization and/or distillation by dissolving it in an organic solvent. In this case, a naphthalenedicarboxylic acid metal salt is separated as an insoluble, and it is supplied to the oxidation of dialkylnaphthalene, etc., according to the present invention 2.

The naphthalenedicarboxylic acid metal salt separated as an insoluble contains almost no trimellitic acid, and only contains NDCM and monomethyl esters of NDCA such as monomethyl 2,6-naphthalenedicarboxylate as impurities to some extent, and it effectively works as a catalyst for the oxidation. Further, when the naphthalenedicarboxylic acid metal salt is used as a catalyst, the average particle diameter of an obtained crude NDCA crystals increase, so that the separation of the crystals become easy.

(Step of dissolving crude ester and step of separating insoluble)

The characteristic feature of the present invention 1 is that a crude ester formed by the esterification is dissolved in an aromatic hydrocarbon as a solvent to separate an insoluble.

The above insoluble is separated by a method (A) in which a crude ester formed by the esterification is mixed with an aromatic hydrocarbon, the mixture is heated to dissolve the total amount of NDCM such as 2,6-NDCM contained in the crude ester in the aromatic hydrocarbon, and then the insoluble contained in the crude ester is separated by filtration or centrifugal precipitation, or by a method (B) in which a crude ester formed by the esterification is distilled under reduced pressure to separate it into a fraction of NDCM such as 2,6-NDCM having an increased concentration and concentrated contents having high boiling points such as catalyst metals, monomethyl 2,6-naphthalenedicarboxylate and organic impurities having a high boiling point, then, the contents having high boiling points are dissolved in the above aromatic hydrocarbon solvent and an insoluble containing the catalyst metals are separated and recovered by the same method as that described above.

In the latter method (B), the metal contents are concentrated and the amount of the solvent is decreased, so that the catalyst metals can be recovered with a smaller separator device. The fraction from the distillation is dissolved in an aromatic hydrocarbon solvent and used in the recrystallization step to be described later.

The aromatic hydrocarbon used as the solvent is preferably selected from hydrocarbons having a boiling point in the range of from 100 to 170° C., such as toluene, xylenes and trimethylbenzenes. Toluene and xylenes are particularly preferred. The amount of the solvent is required to be sufficient for dissolving the total amount of NDCM such as 2,6-NDCM contained in the crude ester and for obtaining a sufficient purification effect in the subsequent purification step. However, when it is used excessively, a large-capacity apparatus is required. The amount of the solvent is therefore 2 to 15 times, preferably 3 to 10 times, as large as the weight of the crude ester.

When the aromatic hydrocarbon is used as a solvent, the crude ester can be dissolved, and an insoluble can be separated, at a temperature lower than the boiling point of the solvent, and the dissolving and separation procedures can be carried out with a simple apparatus as compared with a case where methanol is used which requires the dissolving and separation procedures under elevated pressure.

The insoluble recovered by the above method contains almost all of oxidation catalyst metals which have been contained in NDCA used as a raw material for the esterification. In the above insoluble, a major part other than the catalyst metals used for the oxidation and the esterification is composed of NDCA, and it contains almost no trimellitic acid which works as an inhibiting substance against a reaction in the oxidation. The above insoluble can be therefore suitably used as a catalyst source for the oxidation.

The above insoluble is used as a catalyst source for the oxidation by a method in which the insoluble is directly supplied to an oxidation reactor while it is in the form of a solid or a method in which the insoluble is mixed with water or a lower aliphatic carboxylic acid containing water (preferably acetic acid containing at least 1% by weight of water) to elute oxidation catalyst metals, the mixture is separated into a solid and a liquid, a crystal is removed and a mother liquor is supplied to the oxidation.

(Recrystallization step)

When the above method (A) is employed, the purification of NDCM by recrystallization is carried out as follows. NDCM such as 2,6-NDCM is purified by cooling the aromatic hydrocarbon solution containing the crude ester from which insoluble catalyst metal contents have been removed, to precipitate crystals of NDCM such as 2,6-NDCM and separating the solution into the crystals and a mother liquor by filtration or centrifugal precipitation.

When the above method (B) is employed, the recrystallization is carried out in the following two procedures. In one procedure, the crude ester formed by the esterification is distilled under reduced pressure to remove contents having high boiling points and NDCM such as 2,6-NDCM as a distillate is purified by recrystallization from an aroamtic hydrocarbon solvent, and in the other procedure, contents having high boiling points are mixed with an aromatic hydrocarbon solvent, the mixture is heated to dissolve the contents having high boiling points in the aromatic hydrocarbon solvent, the resultant aromatic hydrocarbon solution is filtered or centrifugalized to remove an insoluble, and the remaining solution is cooled to precipitate crystals.

The temperature for the above recrystallization is preferably in the range of from 20 to 70° C. The recrystallization can be carried out by any one of a batch method and a continuous method. In a batch method, the rate of cooling the solution is preferably 20° C./minute or smaller, and in the continuous method, at least two crystallization vessels are preferably used to precipitate crystals stepwise.

Separated crystals may be re-dissolved in a solvent as required and recrystallized to obtain crystals having a higher purity. In this case, a separated mother liquor obtained by recrystallization in the above second step is used as a solvent in the step of dissolving the product formed by the above esterification, whereby the purification by recrystallization in two steps can be carried out without increasing the amount of the solvent.

In the method (B), the mother liquor separated in the recrystallization step can be used as a solvent in the step of dissolving contents having high boiling points obtained by the distillation, and crystals obtained in the step of recovering crystals from the contents having high boiling points can be recycled to the esterification.

(Distillation step)

While the distillation column used for purification by distillation includes a packed column, a plate column and a perforated plate column, it is preferred to use a distillation column having a structure in which a pressure difference between a column top and a column bottom is as small as possible.

The distillation is preferably carried out under a reduced pressure of 1 to 50 mmHg at a temperature between 210 and 280° C. When the temperature for the distillation is lower than 210° C., the distillation is difficult since the vapor pressure of 2,6-NDCM is low. When the above temperature is higher than 280° C., undesirably, 2,6-NDCM is decomposed.

The contents having high boiling point, separated by distillation in the above method (A), contain monomethyl 2,6-naphthalenedicarboxylate and 2,6-NDCA, and the yield in the process can be improved by recycling the above contents having high boiling points to the esterification. Further, the contents having high boiling points, separated by distillation in the above method (B), further contain catalyst components used for the esterification, and part of the contents having high boiling points can be recycled to the esterification.

As explained, the process for the production of high-purity NDCM such as 2,6-NDCM includes a method (A) in which the crude ester from which insoluble catalyst metals are removed is purified by recrystallization and then purified by distillation and a method (B) in which the crude ester is distilled and then purified by recrystallization.

The method (A) comprises ① the step of oxidizing 2,6-dialkylnaphthalene to obtain 2,6-NDCA, ② the step of esterifying the 2,6-NDCA with methanol to obtain a crude ester, ③ the dissolving step of mixing the crude ester with an aromatic hydrocarbon solvent and heating the mixture to dissolve 2,6-NDCM of the crude ester in the aromatic hydrocarbon solvent, ④ the step of treating a solution of the crude ester in the aromatic hydrocarbon solvent by filtration or precipitation to separate and remove an insoluble of the crude ester, ⑤ the recrystallization step of cooling the resultant insoluble-free solution to precipitate crystals of 2,6-NDCM and separating the solution into a solid and a liquid to obtain recrystallized 2,6-NDCM and ⑥ the distillation step of distilling the recrystallized 2,6-NDCM under reduced pressure to remove contents having high boiling points and obtain high-purity 2,6-NDCM.

The method (B) comprises ① the step of oxidizing 2,6-dialkylnaphthalene to obtain 2,6-NDCA, ② the step of esterifying the 2,6-NDCA with methanol to form a crude ester, ③ the step of distilling the crude ester under reduced pressure to remove contents having high boiling points, ④ the step of recrystallizing 2,6-NDCM as a distillate from an aromatic hydrocarbon solvent to obtain high-purity 2,6-NDCM, ⑤ the dissolving step of mixing the contents having high boiling points, separated by the distillation, with an aromatic hydrocarbon solvent and heating the mixture to dissolve the contents having high boiling points in the aromatic hydrocarbon solvent, ⑥ the step of treating a solution of the contents having high boiling points in the aromatic hydrocarbon by filtration or precipitation to separate and remove insolubles, and ⑦ the crystal recovery step of cooling the resultant insoluble-free solution to precipitate crystals and separating the crystals from the solution.

In any of the above two methods, there can be obtained 2,6-NDCM having a low inorganic impurity content and a low acid value and having an excellent color value and excellent qualities, and effective components of the oxidation catalyst can be effectively recovered.

FIG. 1 shows an example of flow chart of a case according to the method (A), where a crude ester from which insoluble catalyst metals are removed is purified by recrystallization and then crystals are purified by distillation. In FIG. 1, 2,6-dialkylnaphthalene is introduced into an oxidation reactor 1 through a line 11, and a solvent of the oxidation and a catalyst are introduced into the oxidation reactor 1 through a line 12. In the oxidation reactor 1, an oxygen-containing gas (air) is introduced through a line 13, the 2,6-dialkylnaphthalene is oxidized, and an off-gas is discharged through a line 15. 2,6-NDCA formed by the oxidation is introduced into a solid-liquid separator 2 through a line 14, and separated 2,6-NDCA is dried with dryer 3 and introduced into an esterification reactor 4 through a line 18. A liquid separated in the solid-liquid separator 2 is recycled to the oxidation reactor 1 through a line 17.

In the esterification reactor 4, 2,6-NDCA is esterified with methanol introduced through a line 19, and unreacted methanol and formed water are discharged through a line 20. A crude ester from the esterification reactor 4 is introduced into an ester-dissolving vessel 5 through a line 21, and dissolved in an aromatic hydrocarbon solvent introduced from a line 22. The resultant crude ester solution is introduced into a solid-liquid separator 6 through a line 23, and an insoluble containing catalyst components is recycled to the oxidation reactor 1 through a line 25. A liquid separated in the solid-liquid separator 6 is introduced into a solid-liquid separator 8 through a line 24 and a crystallization vessel 7 to be separated into a recrystallization separated cake which is to be introduced into a dryer 9 through a line 26 and a separated liquid from a line 27. The recrystallization separated cake is dried in the dryer 9 and introduced into a distillation column 10, and high-purity 2,6-NDCM as a product is obtained as a distillate through a line 28. Contents having high boiling points, separated in the distillation column 10, are recycled to the esterification reactor 4 through a line 29.

Figure 2:
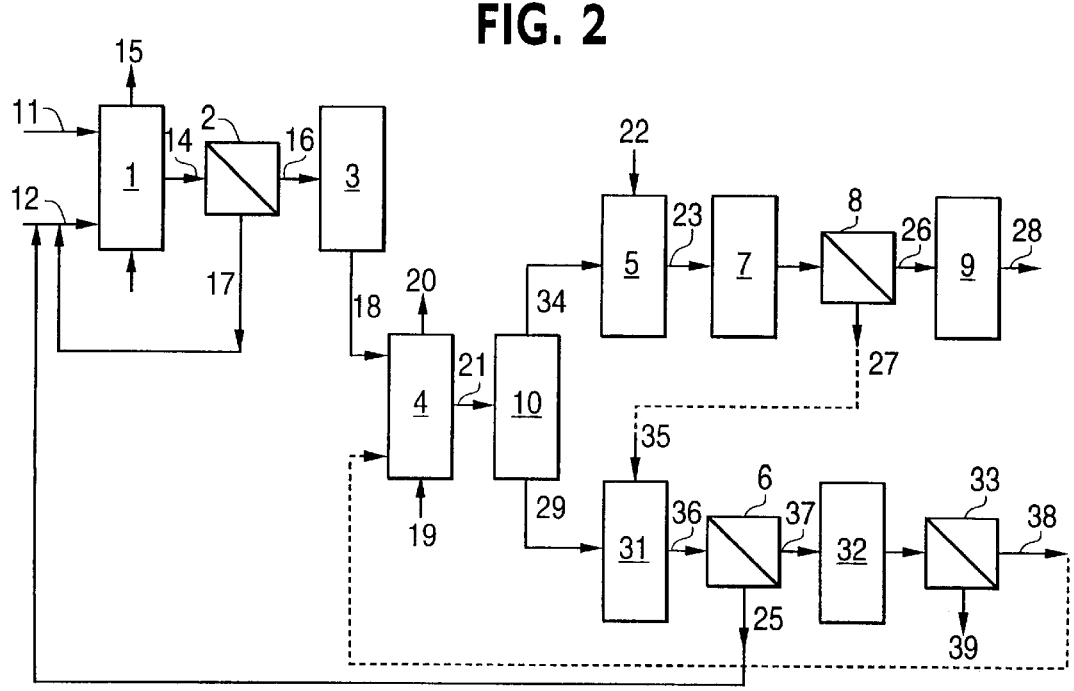
FIG. 2 shows a flow chart of a case where a crude ester is distilled and then purified by recrystallization according to a method (B) in the present invention 1.

FIG. 2 shows an example of flow chart of a case according to the method (B), where a crude ester is distilled and the purification is carried out by recrystallization. In FIG. 2, 2,6-dialkylnaphthalene as a raw material is introduced into an oxidation reactor 1 through a line 11, and a solvent for the oxidation and a catalyst are introduced into the oxidation reactor 1 through a line 12. In the oxidation reactor 1, an oxygen-containing gas (air) is introduced through a line 13, the 2,6-dialkylnaphthalene is oxidized, and an off-gas is discharged through a line 15. 2,6-NDCA formed by the oxidation is introduced into a solid-liquid separator 2 through a line 14, and separated 2,6-NDCA is dried in a dryer 3 and introduced into an esterification reactor 4 through a line 18. A liquid separated in the solid-liquid separator 2 is recycled to the oxidation reactor 1 through a line 17.

In the esterification reactor 4, 2,6-NDCA is esterified with methanol introduced through a line 19, and unreacted methanol and formed water are discharged through a line 20. A crude ester formed in the esterification reactor 4 is introduced into an ester distillation column 10 through a line 21. A distillate from the ester distillation column 10 is introduced into an ester-dissolving vessel 5 through a line 34, and dissolved in an aromatic hydrocarbon solvent introduced through a line 22. The resultant solution is introduced into a solid-liquid separator 8 through a line 23 and a crystallization vessel 7. In the solid-liquid separator 8, the solution is separated to a recrystallization-separated cake to be sent through a line 26 and a separated liquid to be sent through a line 27. The recrystallization-separated cake is dried in a dryer 9, and high-purity 2,6-NDCM as a product is obtained through a line 28.

Contents having high boiling points, i.e., residue, in the ester distillation column 10 are introduced into an ester 31 through a line 29 and dissolved in an aromatic hydrocarbon solvent from a line 35 (separated liquid from the line 27), and the resultant solution is introduced into a solid-liquid separator 6 through a line 36. In the solid-liquid separator 6, an insoluble containing catalyst components is recycled to the oxidation reactor 1 through a line 25. A separated liquid from the solid-liquid separator 6 introduced into a crystallization vessel 32 and a solid-liquid separator 33 through a line 37, and recovered crystals are recycled to the esterification reactor 4 through a line 38.

According to the present invention 1, there is provided a process which enables the production of remarkably high-purity dimethyl 2,6-naphthalenedicarboxylate from a crude ester obtained by the esterification of 2,6-naphthalenedicarboxylic acid with methanol. According to the production process provided by the present invention 1, further, catalyst metals used for the oxidation are recovered at high yields and can be recycled to the oxidation. Therefore, dimethyl 2,6-naphthalenedicarboxylate can be remarkably industrially advantageously produced according to the present invention 1, and the present invention 1 is industrially highly significant.

According to the present invention 2, there is provided a process which enables the production of an NDCA crystal having a large particle diameter and therefore having excellent filterability by using a naphthalenedicarboxlic acid metal salt in the form of a solid as a catalyst component for the oxidation. According to the process provided by the present invention 2, further, the naphthalenedicarboxylic acid metal salt can be easily recovered from the step of esterifying naphthalenedicarboxylic acid and can be also recycled, so that naphthalenedicarboxylic acid can be industrially advantageously produced.

EXAMPLES

The present invention will be more specifically explained with reference to Examples hereinafter. However, the present invention shall not be limited by these Examples.

Table 1 shows measurement values of solubility of 2,6-NDCM in various solvents. It is shown that as compared with the solubility of 2,6-NDCM in aromatic hydrocarbons, the solubility of 2,6-NDCM in methanol at the boiling point of methanol is very low.

TABLE 1

| Solvent | Normal boiling point | Solubility of 2,6-NDCM at a boiling point |
| --- | --- | --- |
| Methanol | 65° C. | 0.67 g/100 g solvent |
| Toluene | 111° C. | 17.5 g/100 g solvent |
| m-Xylene | 139° C. | 40 g/100 g solvent |
| o-Xylene | 144° C. | 52 g/100 g solvent |

EXAMPLE 1

Method (A)

(1) Oxidation

Cobalt acetate tetrahydrate, manganese acetate tetrahydrate, a 47 wt % hydrogen bromide aqueous solution and water were mixed with, and dissolved in 250 kg of glacial acetic acid to obtain a catalyst solution having a cobalt concentration of 0.1% by weight, a manganese concentration of 0.6% by weight, a bromine concentration of 0.5% by weight and a water concentration of 3% by weight.

A 60-liter reactor made of titanium and equipped with a stirrer and a reflux condenser was charged with 32 kg of the above catalyst solution with a pump. Further, a vessel other than the reactor was charged with the catalyst solution of 2,6-dimethylnaphthalene having a purity of 99.7% by weight, and 2,6-dimethylnaphthalene was melted under heat at a temperature of 120° C. or higher.

The pressure inside the reactor was adjusted to 20 kg/cm$^2$G with nitrogen, and the catalyst solution was heated to 210° C. with stirring. After the temperature and the pressure were stabilized, 2,6-dimethylnaphthalene was supplied to the reactor at a rate of 6 kg/hour, and at the same time, compressed air was supplied to the reactor at a rate of about 17 Nm3/hour to initiate an oxidation. When 2,6-dimethylnaphthalene was supplied up to an amount of 8 kg (80 minutes after the initiation of the reaction), the supply of the above catalyst solution was initiated at a rate of 24 kg/hour, and a reaction product was withdrawn to a receiving vessel under atmospheric pressure such that the liquid level in the reactor was constant.

The reaction was continued for about 8 hours, the supply of 2,6-dimethylnaphthalene, the catalyst solution and air was terminated to finish the reaction. A product remaining in the reactor was also withdrawn to the receiving vessel, to give 295 kg of a reaction product.

The above reaction product was separated into a cake and a mother liquor with a decanter type centrifugal separator. The separated cake was dried to give 74.8 g of crude 2,6-NDCA crystals. The liquid content of the separated cake, calculated on the basis of a drying loss, was 39% by weight (based on wet weight). Table 2 shows composition of the crude 2,6-NDCA.

The yield of the 2,6-NDCA on the basis of the supplied 2,6-dimethylnaphthalene was 92.3 mol %. Further, 48% by weight of the catalyst metals (total of cobalt and manganese) used for the reaction remained in the formed crude 2,6-NDCA crystals.

TABLE 2

| composition of crude 2,6-NDCA | wt % |
| --- | --- |
| 2,6-NDCA | 94.8 |
| 2-formyl-6-naphthoic acid | 0.29 |
| Trimellitic acid | 2.4 |
| Cobalt | 0.098 |
| Manganese | 0.93 |

(2) Esterification

A 6-liter autoclave made of stainless steel and equipped with a stirrer was charged with 1.2 kg of the crude 2,6-NDCA obtained by the oxidation, 3.6 kg of a crude ester obtained by esterifying the above crude 2,6-NDCA in advance, and 1.2 g of molybdenum trioxide, and after nitrogen substitution, the contents in the autoclave were heated to 270° C. with stirring.

Methanol was supplied from a nozzle positioned in a bottom portion of the reactor at a rate of 1.06 kg/hour, to initiate an esterification. When the pressure reached 15 kg/cm$^2$G, excess methanol and formed water were withdrawn through a vapor-withdrawing line provided in an upper portion of the reactor, and the reaction was continued for about 3 hours while maintaining the pressure at a constant level.

After completion of the reaction, a crude ester was withdrawn. Further, an ester content withdrawn out of the reactor together with methanol vapor was recovered in the form of crystals by evaporating the methanol. The total amount of the crystals recovered from the methanol and the crude ester in a molten state was 4.93 kg. Table 3 shows the composition of the so-obained crude ester. The yield of the 2,6-NDCM was 92.8 mol %.

TABLE 3

| Composition of crude ester | wt % |
| --- | --- |
| 2,6-NDCM | 89.3 |
| Monomethyl 2,6-naphthalenedicarboxylate | 1.9 |
| 2,6-NDCA | 3.8 |
| Methyl 2-formyl-6-naphthoate | 0.13 |
| Trimethyl trimellitate | 2.3 |
| Cobalt | 0.088 |
| Manganese | 0.83 |
| Molybdenum | 0.057 |

(3) Dissolving of crude ester and separation of insolubles

A 700-mesh filter made of a metal was set in a liquid-withdrawing tubing of an autoclave equipped with a stirrer, to use the autoclave as a pressure filter device. The above autoclave was charged with 800 g of the crude ester obtained by the above esterification and 4,000 g of o-xylene as a solvent. The mixture in the autoclave was heated to about 120° C. with stirring and maintained for about 30 minutes, and then the pressure inside the autoclave was elevated to about 1 kg/cm$^2$G with nitrogen.

The valve of the liquid-withdrawing tubing was opened, and an ester solution was filtered. After completion of the filtering, an insoluble collected with the filter was washed with 400 g of o-xylene which was heated to 120° C. The wash liquid was mixed with the ester solution which had been filtered.

The insoluble collected with the filter was dried to give 41.8 g of crystals. Table 4 shows the composition of the obtained insolubles. The insolubles contained cobalt and manganese in an amount of at least 98% by weight based on the cobalt and manganese which had been contained in the crude 2,6-NDCA used as a raw material for the esterification.

TABLE 4

| Composition of insoluble | wt % |
| --- | --- |
| Cobalt | 1.68 |
| Manganese | 15.8 |
| Molybdenum | 1.0 |
| 2,6-NDCA | 71.8 |
| Monomethyl 2,6-naphthalenedicarboxylate | 1.7 |
| 2,6-NDCM | 1.4 |
| Trimellitic acid | 0.16 |

(4) Recrystallization

The crude ester solution from which the insoluble had been filtered off in the above (3) was cooled to 40° C. with stirring, to precipitate crystals. Precipitated crystals were separated from a mothor liquor by filtration with a glass filter by means of suction. The resultant cake was washed with about 800 g of o-xylene and then dried. The dry weight of the crystals were 697 g, and the liquid content of the cake, calculated on the basis of a dry loss, was 11% by weight based on the weight of a wet cake.

(5) Distillation

The ester crystals obtained by the recrystallization was purified by distillation according to a batch method. The distillation was carried out with a 10-stage distillation column under a condition where the column top pressure was set at 16 mmHg, to give purified 2,6-NDCM at a distillate amount ratio of 89% by weight based on the weight of charged crystals. Concerning the qualities of the obtained purified 2,6-NDCM, it had an organic impurity content of 0.028% by weight and an acid value of 0.004 mg-KOH/g.

EXAMPLE 2

Purified 2,6-NDCM was obtained from the same crude ester as that obtained by the esterification in Example 1 by carrying out the dissolving of the crude ester, the separation of insolubles, crystallization and distillation in the same manner as in Example 1 except that the o-xylene used as a solvent in the dissolving step and as a wash liquid for washing a separated cake in the recrystallization step was replaced with toluene.

Table 5 shows the liquid content of a cake obtained by the recrystallization and the product qualities of the purified 2,6-NDCM obtained by the distillation.

COMPARATIVE EXAMPLE 1

Purified 2,6-NDCM was obtained from the same crude ester as that obtained by the esterification in Example 1 in the same manner as in Example 1 except that the o-xylene used as a solvent in the dissolving step and as a wash liquid for washing a separated cake in the recrystallization step was replaced with methanol. In addition, the heating temperature for dissolving the entire amount of 2,6-NDCM in the step of dissolving the crude ester was required to be 130° C., and the pressure in this case was about 7 kg/cm$^2$G.

Table 5 shows the liquid content of a cake obtained by the recrystallization and the product qualities of the purified 2,6-NDCM obtained by the distillation. As a characteristic impurity, there was found anhydrous monomethyl trimellitate which it is considered had been formed from trimethyl trimellitate which had not been removed by the recrystallization and had been decomposed during the distillation.

EXAMPLE 3

Method (B)

800 Grams of the same crude ester as that obtained by the esterification in Example 1 was distilled under a reduced pressure of 16 mmHg by a batch method using the same distillation column as that used in Example 1, to give 664 g of a distillate. The distillate was dissolved in 4,000 g of m-xylene and then recrystallized in the same manner as in Example 1, to give purified 2,6-NDCM. Table 5 shows the liquid content of a cake in the recrystallization and the product qualities of the purified 2,6-NDCM.

Further, the residue from the above distillation was dissolved, under heat, in 2,000 g of a separated mother liquor obtained by the recrystallization of the distillate together with an ester remaining in the distillation column, and a residue solution was taken out of the distillation column. The residue solution was charged into the same pressure filter as that used in Example 1, and an insoluble was separated in the same manner as in Example 1. The insoluble had a dry weight of 43.3 g, and its composition was as shown in Table 6. In the above method, at least 98% by weight, based on the cobalt and manganese contained in the crude 2,6-NDCA used as a raw material for the esterification, of cobalt and manganese were contained in the insoluble.

TABLE 5

|  | Ex. 2 | CEx. 1 | Ex. 3 |
| --- | --- | --- | --- |
| Liquid content of cake separated by recrystallization (based on wet product) | 13 wt % | 28 wt % | 10 wt % |
| Product qualities of purified NDCM |  |  |  |
| Content of organic impurity | 0.033 | 0.087 | 0.035 |
| Acid value (mg-KOH/g) | 0.005 | 0.048 | 0.005 |

Ex. =Example, CEx. =Comparative Example

TABLE 6

| Composition of insolubles | wt % |
| --- | --- |
| Cobalt | 1.61 |
| Manganese | 15.3 |
| Molybdenum | 1.0 |
| 2,6-NDCA | 71.6 |
| Monomethyl 2,6-naphthalenedicarboxylate | 2.7 |
| 2,6-NDCM | 1.3 |
| Trimellitic acid | 0.0 |

COMPARATIVE EXAMPLE 2

Cobalt acetate tetrahydrate, manganese acetate tetrahydrate, a 47 wt % hydrogen bromide aqueous solution and water were mixed with, and dissolved in, 287 g of glacial acetic acid, to obtain 300 g of a catalyst solution having a cobalt concentration of 0.05% by weight, a manganese concentration of 0.3% by weight, a bromine concentration of 0.25% by weight and a water contentration of 3% by weight.

A 500-ml autoclave made of titanium and equipped with a stirrer, a reflux condenser and a raw material feeding pump was charged with 112 g of the above catalyst solution. The remaining catalyst solution in an amount of 188 g was mixed with 37.5 g of 2,6-dimethylnaphthalene, and the mixture was charged into a raw material supply vessel and heated to dissolve the dimethynaphthalene, whereby a raw material solution was obtained.

The pressure inside the autoclave was adjusted to 18 kg/cm$^2$G with nitrogen, and the catalyst solution was heated to 200° C. with stirring. After the temperature and the pressure were stabilized, 2,6-dimethylnaphthalene, the catalyst solution and compressed air were supplied to the autoclave to initiate an oxidation. While the flow rate of supplied air was adjusted such that discharged gas had an oxygen concentration of 2% by volume, the raw material solution was continuously supplied over 1 hour. After completion of the supply of the raw material solution, the supply of air was continued until discharge gas had an oxygen concentration of 10% by volume.

After completion of the reaction, the autoclave was cooled to room temperature, and a reaction production was withdrawn and filtered through a glass filter by means of suction to separate a crystal. The separated cake was measured for a weight and dried with a dryer to give 50.7 g of crude 2,6-NDCA crystals. Table 7 shows the composition of the crude 2,6-NDCA and the yield of 2,6-NDCA based on the supplied 2,6-dimethylnaphthalene.

EXAMPLE 4

Recovery and recycle of oxidation catalyst metals 2,6-Dimethylnaphthalene was oxidized under the same conditions as those in Comparative Example 2 with the same procedures as those in Comparative Example 2 except that the same insoluble containing oxidation catalyst metals as that separated and recovered from the solution of the crude ester in o-xylene in Example 1 was used as part of cobalt and manganese sources. The amount of the insoluble used for the preparation of a catalyst solution was 3.0 g, and cobalt acetate tetrahydrate and manganese acetate tetrahydrate were used as supplements for deficient metal contents for adjusting the catalyst concentration to a predetermined value.

The weight of a dry crystal of the obtained crude 2,6-NDCA was 53.2 g. Table 7 shows the composition of the crude 2,6-NDCA and the yield of the 2,6-NDCA based on the supplied 2,6-dimethylnaphthalene. In the calculation of the yield, the content of 2,6-NDCA in the insoluble was deducted from the amount of 2,6-NDCA contained in the reaction product.

EXAMPLE 5

3 Grams of the insoluble containing oxidation catalyst metals separated and recovered from the o-xylene solution of the crude ester in Example 1 was mixed with 60 g of acetic acid containing 30% by weight of water, and the mixture was stirred at 80° C. for 20 minutes and then fractionated to crystals and a filtrate with a glass filter. Concerning the transfer of metal contents into the filtrate, the transfer ratio of cobalt was 98.1%, the transfer ratio of manganese was 95.4%, and the transfer ratio of molybdenum was 11.5%.

The mother liquor from which the metal contents had been extracted was heated to evaporate the solvent and concentrate it. Then, 2,6-dimethylnaphthalene was oxidized under the same conditions as those in Comparative Example 2 and with the same procedures as those in Comparative Example 2 except that the above obtained concentrated solution was used as part of cobalt and manganese sources for the preparation of a catalyst solution. In addition, cobalt acetate tetrahydrate and manganese acetate tetrahydrate were used as supplements for deficient metal contents for adjusting the catalyst concentration to a predetermined value.

The weight of dry crystals of the obtained crude 2,6-NDCA was 50.8 g. Table 7 shows the composition of the crude 2,6-NDCA and the yield of the 2,6-NDCA based on the supplied 2,6-dimethylnaphthalene.

TABLE 7

| Composition (wt %) | CEx. 2 | Ex. 4 | Ex. 5 |
|---|---|---|---|
| 2,6-NDCA | 95.1 | 94.0 | 94.8 |
| 2-formyl-6-naphthoic acid | 0.24 | 0.21 | 0.25 |
| Trimellitic acid | 2.2 | 2.8 | 2.3 |
| Yield of 2,6-NDCA (mol %) | 93.3 | 92.5 | 93.1 |

In Examples and Comparative Example to be described later, the definition of yield of NDCA and the method of measurement of a crystal size are as follows.

① Yield of NDCA

When naphthalenedicarboxylic acid metal salt is recovered from NDCM, NDCM, NDCA and monomethyl naphthalenedicarboxylate (these three components will be referred to as "NDCA content" hereinafter) obtained in the naphthalenedicarboxylic acid metal salt are excluded from the calculation of an yield, and the yield is calculated in terms of molar ratio. That is, Yield (%) of NDCA=[(NDCA content in formed product)−NDCA content in added materials]]/(supply amount of DMM)

② Method of measurement of crystal size

A laser-diffraction-applied particle size distribution measuring apparatus was used, and a 50% value of accumulated distribution of particle sizes of crystals was taken as an average particle size of the crystals. As an amount ratio of crystallites, an amount ratio of a crystal having a size of 10 $\mu$m or smaller was determined.

EXAMPLE 6

2.09 Grams of the NDCA metal salt obtained in Example 1, cobalt acetate tetrahydrate, a 47 wt % hydrogen bromide aqueous solution, glacial acetic acid and water were mixed to prepare a solution having a manganese concentration of 3,000 ppm, a cobalt concentration of 500 ppm, a bromine concentration of 3,000 ppm and a water concentration of 3% by weight. The solution was charged into an autoclave.

The above solution was in the form of a slurry. 50 Grams/hour of 2,6-dimethylnaphthalene and 250 g/hour of a catalyst solution, which was prepared from manganese acetate tetrahydrate, cobalt acetate tetrahydrate, a 47 wt % hydrogen bromide aqueous solution, glacial acetic acid and water so as to have a manganese concentration of 3,000 ppm, a cobalt concentration of 500 ppm, a bromine concentration of 3,000 ppm and a water concentration of 3% by weight, were supplied for 45 minutes, and the 2,6-dimethylnaphthalene was oxidized with air at 18 kg/cm$^2$G at 200° C. A discharged gas had an oxygen concentration of 3% by volume. After 45 minutes, the supply of the raw material and the catalyst solution was terminated, and a post-oxidation was carried out for 6 minutes. A reaction product was withdrawn and separated into a solid and a liquid.

The so-obtained NDCA crystal had a purity of 94.7% by weight and an average particle size of 20 $\mu$m, and the amount ratio of crystals having a particle size of 10 $\mu$m or smaller was 10%. The obtained NDCA crystals therefore had excellent filterability. The yield of the NDCA was 92.3%.

COMPARATIVE EXAMPLE 3

A catalyst solution was prepared from cobalt acetate tetrahydrate and manganese acetate tetrahydrate without using the NDCA metal salt obtained in Example 1, and an oxidation was carried out under the same conditions as those in Example 6.

The so-obtained NDCA crystals had a purity of 95.2% by weight and an average particle diameter of 10 $\mu$m. The amount ratio of crystals having a diameter of 10 $\mu$m or less was 49%, i.e., the ratio of crystallites was large so that the NDCA crystals had poor filterability. The yield of the NDCA was 92.4%.

EXAMPLE 7

An oxidation was carried out under the same conditions as those in Example 6 except that the amount of the NDCA metal salt was changed to 0.80 g and that manganese acetate tetrahydrate and cobalt acetate tetrahydrate were used as supplements for deficient metal contents.

The so-obtained NDCA crystals had a purity of 94.6% by weight and an average particle size of 17 $\mu$m, and the amount ratio of crystals having a particle size of 10 $\mu$m or smaller was 16%, or the amount ratio of crystallites was small. The obtained NDCA crystals therefore had excellent filterability. The yield of the NDCA was 92.4%.

EXAMPLE 8

An oxidation was carried out under the same conditions as those in Example 6 except that the amount of the NDCA metal salt was changed to 1.45 g and that manganese acetate tetrahydrate and cobalt acetate tetrahydrate were used as supplements for deficient metal contents.

The so-obtained NDCA crystal had a purity of 94.8% by weight and an average particle size of 27 $\mu$m, and the amount ratio of crystals having a particle size of 10 $\mu$m or smaller was 18%, or the amount ratio of crystallites was small. The obtained NDCA crystals therefore had excellent filterability. The yield of the NDCA was 92.5%.

COMPARATIVE EXAMPLE 4

An oxidation was carried out under the same conditions as those in Example 8 except that there was used an extract which was prepared by stirring a solution of 1.45 g of the NDCA metal salt in Example 8 in 20 g of a 50% acetic acid aqueous solution at 80° C. for 30 minutes and extracting catalyst component cobalt and manganese. The ratio of extraction of cobalt was 96.4%, and the above ratio of manganese was 98.7%.

The so-obtained NDCA crystals had a purity of 94.5% by weight and an average particle diameter of 12 $\mu$m. The amount ratio of crystals having a diameter of 10 $\mu$m or less was 45%, i.e., the amount ratio of crystallites was large so that the NDCA crystals had poor filterability. The yield of the NDCA was 92.5%.

EXAMPLE 9

The NDCA metal salt obtained in Example 1, acetic acid, cobalt acetate tetrahydrate, manganese acetate tetrahydrate, a 47 wt % hydrogen bromide aqueous solution and water were mixed to obtain a catalyst solution having a cobalt concentration of 0.1% by weight, a manganese concentration of 0.6% by weight, a bromine concentration of 0.5% by weight and a water concentration of 3% by weight, and the catalyst solution was also adjusted such that the amount ratio of the NDCA metal salt based on the catalyst solution was 1.25% by weight. 720 Grams/hour of the catalyst solution and 120 g of 2,6-dimethylnaphthalene having a purity of 99.4% by weight were charged. The 2,6-dimethylnaphthalene was oxidized with air at 210° C. at 20 kg/cm$^2$G while a reaction mixture was continuously withdrawn such that a resistance time was 60 minutes.

The so-obtained reaction mixture was separated into a solid and a liquid. The obtained NDCA crystals had a purity of 95.5% by weight and an average particle diameter of 25 μm. The amount ratio of crystals having a diameter of 10 μm or smaller was 15%, or the amount of crystallites was small, and the NDCA crystals had excellent filterability. The yield of the NDCA was 92.5%.

COMPARATIVE EXAMPLE 5

An oxidation with air was carried out under the same conditions as those in Example 9 by replacing the NDCA metal salt with cobalt acetate tetrahydrate and manganese acetate tetrahydrate.

The so-obtained NDCA crystals had a purity of 95.7% by weight and an average particle diameter of 12 μm. The amount ratio of a crystals having a diameter of 10 μm or less was 43%, i.e., the amount ratio of crystallites was large so that the NDCA crystals had poor filterability. The yield of the NDCA was 92.5%.

What is claimed is:

1. A process for the production of high-purity dimethyl 2,6-naphthalenedicarboxylate, which comprises: esterifying 2,6-naphthalenedicarboxylic acid obtained by liquid phase oxidation of 2,6-dialkylnaphthalene with molecular oxygen in the presence of an oxidation catalyst, with methanol by mixing the 2,6-naphthalenedicarboxylic acid with molten dimethyl 2,6-naphthalenedicarboxylate to form a mixture and continuously supplying a vaporized methanol to the mixture to form a crude ester, and then purifying the crude ester by a process which consists essentially of mixing it with an aromatic hydrocarbon solvent to form a solvent-crude ester mixture, heating the solvent-crude ester mixture to dissolve the crude ester in the aromatic hydrocarbon solvent, removing insolubles contained in the solution of the crude ester by filtering or centrifuging, cooling the solution of the crude ester after the removal of the insolubles to recrystallize and separate dimethyl 2,6-naphthalenedicarboxylate crystals, and distilling the separated crystals of dimethyl 2,6naphthalenedicarboxylate under reduced pressure to remove high-boiling fractions therefrom.

2. The process according to claim 1, wherein the fractions having high boiling points are recycled to the esterification.

3. The process according to claim 1, wherein part of a mother liquor separated by the recrystallization is used as a solvent for dissolving the contents having high boiling points.

4. The process according to claim 1, wherein the dimethyl 2,6-naphthalenedicarboxylate crystallized and recovered is recycled to the esterification.

5. The process according to claim 1, wherein the 2,6-dialkylnaphthalene is 2,6-dimethylnaphthalene.

6. The process according to claim 1, wherein the aromatic hydrocarbon has a boiling point in the range of from 100° C. to 170° C.

7. The process according to claim 6, wherein the aromatic hydrocarbon is at least one aromatic hydrocarbon selected from the group consisting of toluene, xylene and trimethylbenzene.

8. The process according to claim 1, wherein the esterification is carried out at a temperature of 190 to 320° C. at a pressure of 2 to 40 kg/cm$^2$G.

9. The process according to claim 1, wherein the liquid phase oxidation of 2,6-dialkylnaphthalene is carried out in the presence of an oxidation catalyst composed of heavy metals containing at least cobalt and manganese and bromine.

10. The process according to claim 1, wherein insolubles in the aromatic hydrocarbon are separated and recovered from the crude ester and the recovered insoluble is recycled as a catalyst source for the oxidation.

11. The process according to claim 10, wherein the insolubles are recycled to the oxidation as is in the form of a solid.

12. The process according to claim 10, wherein the insolubles are mixed with water or a lower aliphatic carboxylic acid solvent containing water, the resultant mixture is stirred to form a solution, contents which are not dissolved are removed and the remaining solution is used as a catalyst source for the oxidation.

13. A process for the production of naphthalenedicarboxylic acid, which comprises oxidizing dialkylnaphthalene and/or its oxide derivative with an oxygen-containing gas in a solvent containing a lower aliphatic carboxylic acid in the presence of an oxidation catalyst composed of heavy metals containing at least cobalt and manganese and bromine, the oxidation being carried out using, as a catalyst component, a naphthalenedicarboxylic acid metal salt in the form of a solid.

14. A process according to claim 13, wherein the naphthalenedicarboxylic acid containing the oxidation catalyst is esterified, and the naphthalenedicarboxylic acid metal salt is recovered from an obtained ester and recycled to the oxidation.

15. A process according to claim 13, wherein the naphthalanedicarboxylic acid metal salt is at least one salt selected from the group consisting of cobalt naphthalenedicarboxylate, manganese naphthalenedicarboxylate, cerium naphthalenedicarboxylate and nickel naphthalenedicarboxylate.

16. A process according to claim 13, wherein the naphthalenedicarboxylic acid metal salt is added in an amount of 0.5 to 20% by weight based on the total amount of the dialkylnaphthalene and/or its oxide derivative.

17. A process for the production of high-purity dimethyl 2,6-naphthalenedicarboxylate, which comprises: esterifying 2,6-naphthalenedicarboxylic acid obtained by liquid phase oxidation of 2,6-dialkylnaphthalene with molecular oxygen in the presence of an oxidation catalyst, with methanol by mixing the 2,6-naphthalenedicarboxylic acid in molten dimethyl 2,6-naphthalenedicarboxylate to form a mixture and continuously supplying a vaporized methanol to the resultant mixture to form a crude ester, then purifying the crude ester by distilling the crude ester formed by the esterification under reduced pressure to remove fractions having high boiling points and form a distillate containing dimethyl 2,6-naphthalenedicarboxylate and recrystallizing said distillate in an aromatic hydrocarbon solvent to form dimethyl 2,6-naphthalenedicarboxylate crystals and a mother liquor.

18. The process according to claim 17, which further comprises mixing the fractions having high boiling points with an aromatic hydrocarbon solvent to form a mixture, heating the mixture to dissolve the mixture in the aromatic hydrocarbon solvent, removing insolubles in solution by a process which consists essentially of filtering or centrifugalizing, cooling the resultant solution free of the insolubles to precipitate crystals of dimethyl 2,6-naphthalenedicarboxylate and recovering the dimethyl 2,6-naphthalenedicarboxylate.

* * * * *